United States Patent
Oslie

(10) Patent No.: US 11,633,088 B2
(45) Date of Patent: Apr. 25, 2023

(54) GRASPING MECHANISM FOR SIDE-LOADING OPTICAL ENDOSCOPES AND ENDOSCOPE CAMERA HEAD WITH ENDOSCOPE EYEPIECE GRASPING MECHANISM

(71) Applicant: KARL STORZ SE & Co. KG, Tuttlingen (DE)

(72) Inventor: Larry Oslie, Tuttlingen (DE)

(73) Assignee: KARL STORZ SE & Co. KG, Tuttlingen (DE)

(*) Notice: Subject to any disclaimer, the term of this patent is extended or adjusted under 35 U.S.C. 154(b) by 65 days.

(21) Appl. No.: 17/346,494

(22) Filed: Jun. 14, 2021

(65) Prior Publication Data
US 2022/0395164 A1 Dec. 15, 2022

(51) Int. Cl.
*A61B 1/00* (2006.01)
*A61B 1/04* (2006.01)

(52) U.S. Cl.
CPC ...... *A61B 1/00195* (2013.01); *A61B 1/00128* (2013.01); *A61B 1/044* (2022.02)

(58) Field of Classification Search
CPC ............ A61B 1/00128; A61B 1/00195; A61B 1/00112; A61B 1/00126; A61B 1/042
See application file for complete search history.

(56) References Cited

U.S. PATENT DOCUMENTS

| | | | |
|---|---|---|---|
| 4,552,131 A * | 11/1985 | Omagari | G02B 23/2453 600/165 |
| 4,740,058 A | 4/1988 | Hori et al. | |
| 5,406,418 A | 4/1995 | Deary | |
| 6,004,263 A * | 12/1999 | Nakaichi | A61B 1/0607 600/179 |
| 2006/0229495 A1 * | 10/2006 | Frith | A61B 1/00126 600/112 |
| 2009/0128934 A1 | 5/2009 | Plangger | |

FOREIGN PATENT DOCUMENTS

JP H11337846 A 12/1999

* cited by examiner

*Primary Examiner* — Aaron B Fairchild
(74) *Attorney, Agent, or Firm* — McGlew and Tuttle, P.C.

(57) ABSTRACT

An endoscope eyepiece grasping mechanism includes a base part with an arcuate wall portion defining a base part wall opening between the base part arcuate wall portion circumferential ends and a rotatable part with a rotatable arcuate wall portion defining a rotatable part arcuate wall opening between the rotatable arcuate wall portion circumferential ends. A path guide rotates and axially moves the rotatable part relative to the base part between an open and closes state. A biasing device acts to bias the rotatable part toward the closed state, whereby an endoscope eyepiece may be pushed through an endoscope eyepiece side opening to a coupled position in the open state and the rotatable part rotates to the closed state and moves axially toward the base to retain the eyepiece in the coupled position.

13 Claims, 9 Drawing Sheets

GRASPING MECHANISM FOR SIDE-LOADING OPTICAL ENDOSCOPES AND ENDOSCOPE CAMERA HEAD WITH ENDOSCOPE EYEPIECE GRASPING MECHANISM

TECHNICAL FIELD

The present invention relates generally to endoscopic camera devices and more particularly relates to a grasping mechanism or coupler to be fixed on a camera head device or similar optical device to couple the device with an optical endoscope such as a side-loading optical endoscope.

TECHNICAL BACKGROUND

Endoscopic devices are used in the medical field for observing inside of a patient's body cavity. Such endoscopic devices include an insertion unit to be inserted into a patient's body cavity, a light source device that supplies light to the insertion unit that shines onto a target of observation and a removable camera head which is coupled to an eyepiece at the base of the endoscope. The camera head may be associated with a control device that controls the camera head as well as a display device that displays images produced by the camera head imaging device such as a CCD, CMOS or similar imaging device.

Camera heads may be provided with a grasping mechanism or coupler to grasp the eyepiece of an endoscope to effectively couple the endoscope to the camera head. The grasping mechanisms typically use multiple parts that require precise machining to provide a twist open and close grasping of the eyepiece. Providing a precision mechanism has entailed high cost with regard to the machining of the multiple parts. Ease-of-use of the grasping mechanism is affected by the structure and the precision of the rotatable parts.

SUMMARY OF THE INVENTION

It is an object of the invention to provide an endoscope eyepiece grasping mechanism which can be provided with a camera head and which can grasp an eyepiece of an endoscope to couple the endoscope to the camera head with a reliable configuration that provides a precision grasping of the eyepiece while avoiding the high costs of precision machining.

It is a further object of the invention to provide a dependable endoscope eyepiece grasping mechanism which is easy to actuate and preferably can be single hand actuated.

According to the invention, an endoscope eyepiece grasping mechanism is provided comprising a base part and a rotatable part. The base part comprises a base portion with a radially inward light passage and an outer surface and a base part arcuate wall portion disposed radially outward of the light passage. The base part arcuate wall portion extends axially from the base portion and extends a circumferential distance between base part arcuate wall portion circumferential ends and defines a base part arcuate wall portion wall opening between the base part arcuate wall portion circumferential ends. The rotatable part comprises an annular portion with a radially inward surface, and a rotatable arcuate wall portion including an axial surface extending axially from the annular portion and including a coupling edge with a radial surface extending radially inwardly from the axial surface. The rotatable arcuate wall portion extends a circumferential distance between rotatable part arcuate wall portion circumferential ends and defines a rotatable part arcuate wall opening between the rotatable arcuate wall portion circumferential ends. A path guide provides guided movement of the rotatable part relative to the base part for moving the rotatable arcuate wall portion relative to the base part between an open state and a closed state. In the open state the rotatable part arcuate wall opening and the base part arcuate wall portion wall opening at least partially overlap to define a eyepiece receiving spacing and with the radial surface spaced from the base portion by a first axial distance to define an endoscope eyepiece side opening. In the closed state the rotatable part arcuate wall opening and the base part arcuate wall portion wall opening do not overlap or overlap to an extent to provide a gap that is smaller than the endoscope receiving spacing and with the radial surface spaced from the base portion by a second axial distance, which second axial distance is smaller than said first axial distance. A biasing device acts to bias the rotatable part toward the closed state. An endoscope eyepiece may be pushed through the endoscope eyepiece side opening to a coupled position in the open state. The rotatable part rotates to the closed state and the radial surface moves axially toward the base position to retain the eyepiece in the coupled position.

The path guide may advantageously comprise a helical groove in the outer surface of the base portion, the helical groove extending circumferentially about at least a portion of a base part outer periphery. A helical race groove may be provided in the radially inward surface of the rotatable part. A ball arrangement may be provided comprising a ball partially disposed in the race groove and partially disposed in the helical groove. The ball, the race groove and the helical groove guide the rotatable part relative to the base part between the open state and the closed state.

The base part may be an injection molded part with the helical groove formed in the outer surface. The rotatable part may be an injection molded part with the race groove formed in the radially inward surface.

A limit configuration may be provided to limit rotation of the rotatable part relative to the base part in each of two rotational directions. The limit configuration advantageously comprises a limit helical groove extending essentially parallel to the helical groove of the rotational part. The limit helical groove may have a limited circumferential extent between a first limit end and a second limit end. A limit ball is provided in the limit helical groove. A limit ball support may support the limit ball relative to the limit helical groove, whereby the movement of rotational part relative to the base part is limited by the travel of the limit ball between the first limit end and the second limit end.

The helical groove may be in the outer surface of the base portion and extend less than 360 degrees about a circumference of the base portion.

The ball configuration or ball arrangement may comprise a plurality of balls partially disposed in the race groove and partially disposed in the helical groove.

The grasping mechanism may further comprise a limit configuration limiting rotation of the rotatable part relative to the base part.

The bias device may comprise one or more compression springs.

The rotatable part has an eyepiece contact surface at one of the arcuate wall portion circumferential ends. With this configuration, the rotatable part arcuate wall opening and the base part arcuate wall portion wall opening overlap to form the gap in the closed state. Upon pressing the endoscope eyepiece toward and through the gap the endoscope eyepiece presses the eyepiece contact surface to rotate the rotatable part towards the open state to allow the endoscope eyepiece to be pushed through the endoscope eyepiece side opening to the coupled position.

The base part may be connected to a camera head chassis.

According to another aspect of the invention, a camera head comprises a camera head chassis and an endoscope eyepiece grasping mechanism having some or all of the features as discussed above. The base part is connected to a camera head chassis.

According to another aspect of the invention, an endoscope system is provided comprising: an endoscope with an endoscope eyepiece and a camera head having some or all of the features as discussed above.

The disclosed devices advantageously are formed of molded parts allowing precision helical grooves to be provided that receive stainless steel balls or other similar relatively low cost friction reducing features to guide the relatively moving parts. Such molded parts can be effectively made to provide a high quality and precision endoscope eyepiece grasping mechanism.

The endoscope eyepiece grasping mechanism is particularly robust and advantageous as to construction with the two piece—top (rotatable part) and bottom (base part) grasping mechanism. The grasping mechanism may be made with low costs, relative to the precision attained, based on injection molded top/bottom with any colors required. A single heat staked pin may engage a single limit ball to capture all components. No lubrication is required based on self-lubricating injection molded plastic for both the top and bottom. The configuration particularly provides the advantage of a single hand top side snap-in insertion endoscope engagement—no second hand is required for insertion of the endoscope. In particular the endoscope may be pressed into the gap in the closed state to rotate the rotatable part (top) at a set spring force using finger/s only. The endoscope friction locks with a clockwise finger rotation with a max. open/close rotation of approximately 72 deg. The configuration provides a smooth rotation through low friction compression spring coil line contact plus a near frictionless point contact only of stainless steel balls.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
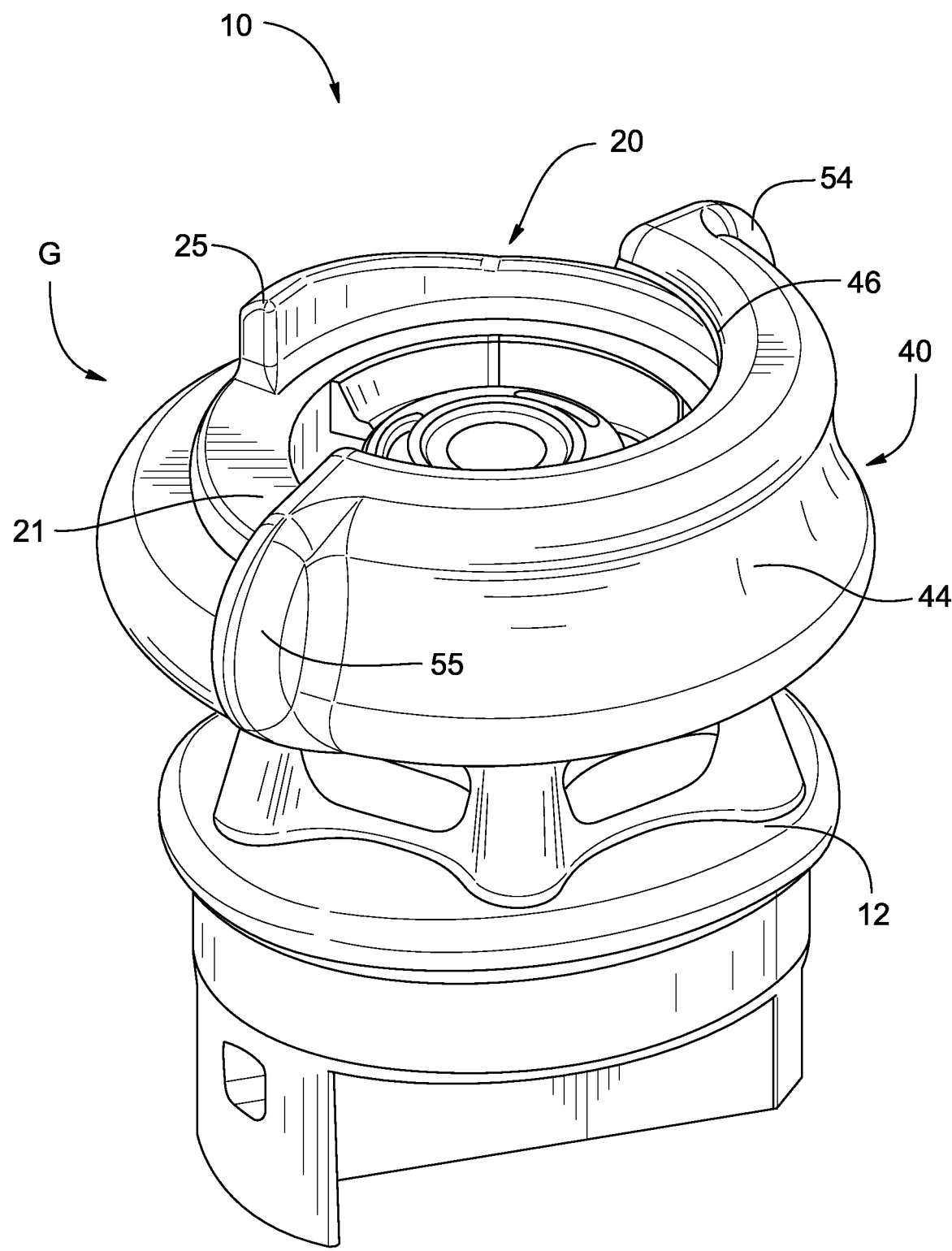
FIG. 1A is a perspective view showing an endoscope eyepiece grasping mechanism in a closed state and with features according to the invention.

Referring to the drawings, FIG. 1A shows a grasping mechanism generally designated 10, which is attached to a mounting portion 12 of a camera head chassis 2. The grasping mechanism 10 comprises a base part 20 and a rotatable part 40. The rotatable part 40 rotates about the base part 20. The base part 20 attaches to the camera chassis 2 in a central region at the mounting portion 12, via a threaded retaining nut or other known fastening mechanism.

FIG. 1A shows the grasping mechanism 10 in a closed state or grasping position. In this closed state an endoscope eyepiece 6 (FIGS. 7-9), disposed in an interior region 14 of the grasping mechanism 10, is in a coupled position and is grasped by the grasping mechanism 10, to couple the endoscope eyepiece 6 to the camera head 2. In this closed state, the grasping mechanism 10 partially surrounds a periphery of the endoscope eyepiece 6 that is disposed in the central interior region 14, to prevent radial displacement from the coupled position and also clamps the endoscope eyepiece 6 in an axial direction to prevent axial displacement of the endoscope eyepiece 6 out of the coupled position.

Figure 1B:
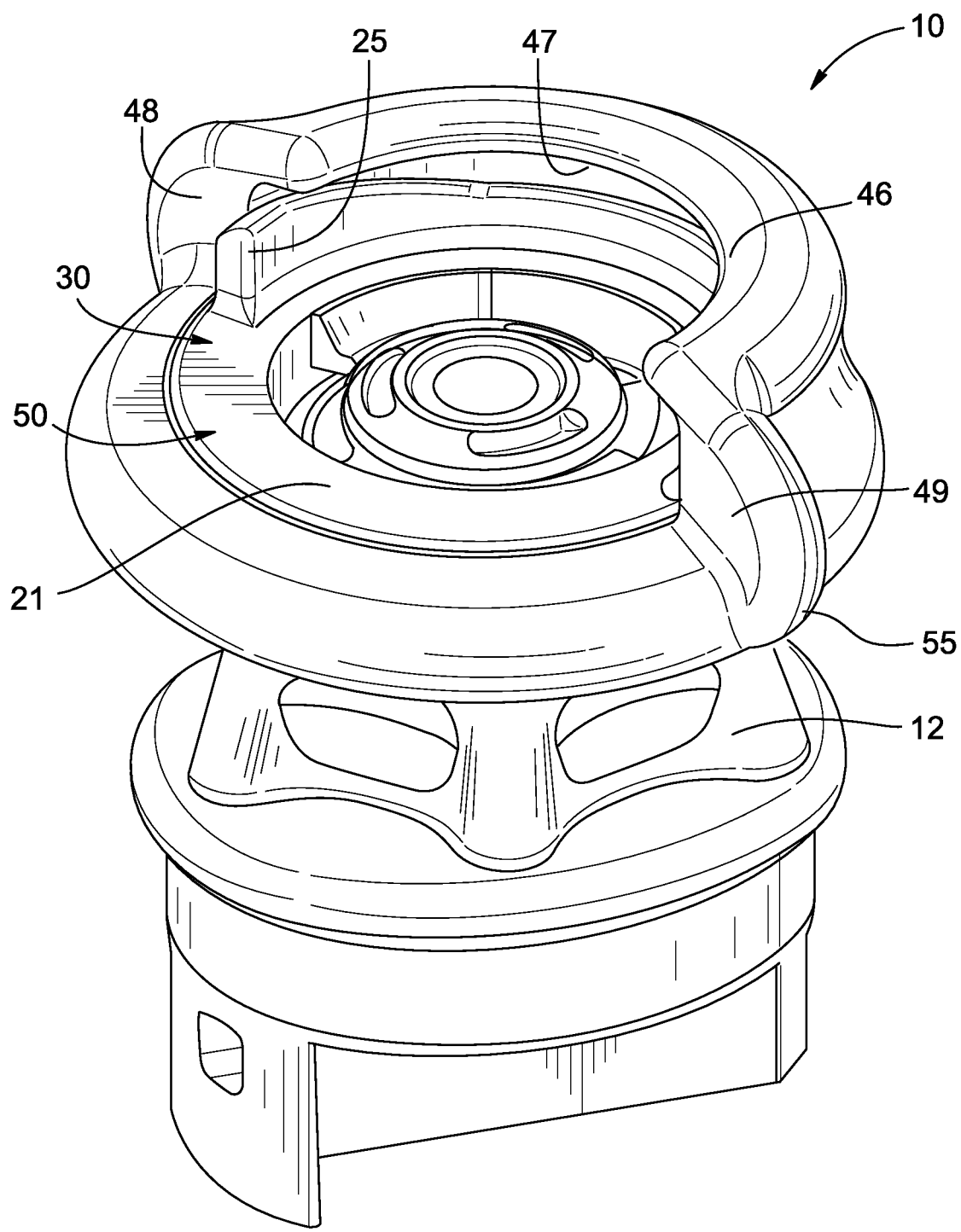
FIG. 1B is a perspective view showing the endoscope eyepiece grasping mechanism in an open state.
Figure 7:
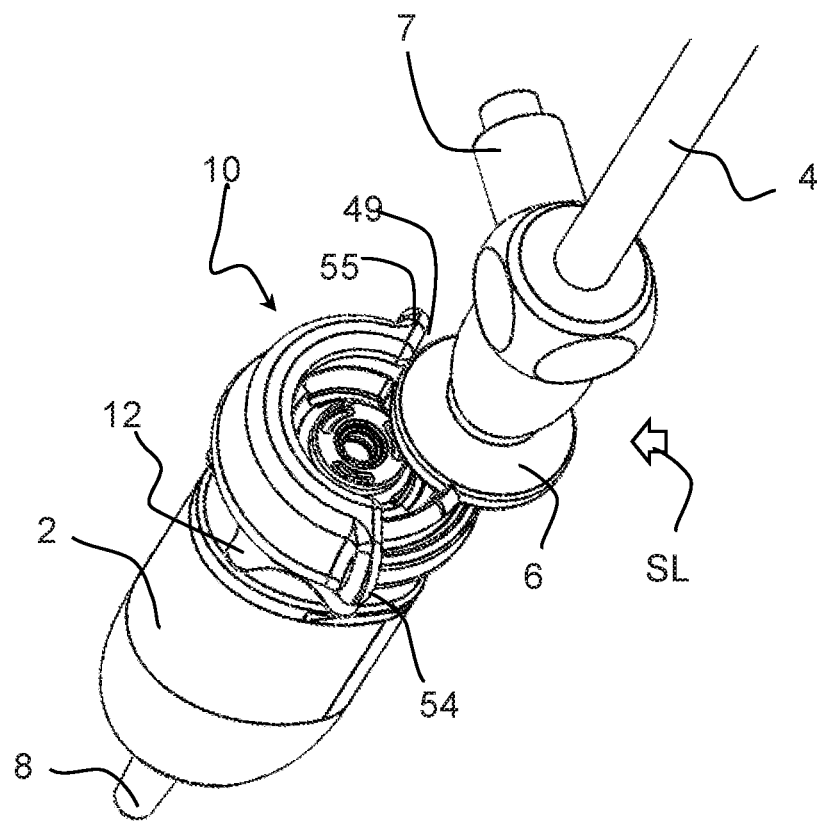
FIG. 7 is a perspective view showing a snap in action insertion of an endoscope, having an endoscope eyepiece, into the grasping mechanism of a camera head.

FIG. 1B shows the grasping mechanism 10 in an open state or loading position. In this open state the endoscope eyepiece 6 may be inserted into the interior region 14 of the grasping mechanism 10 by passing the eyepiece 6 through a base part arcuate wall portion wall opening 30 and through a rotatable part arcuate wall opening 50, which openings overlap, at least to some degree, in this open state. The endoscope eyepiece 6 is moved laterally into the interior region 14 of the grasping mechanism 10 to the coupled position (FIG. 7). The grasping mechanism 10 is then actuated, namely allowed to transition from the open state shown in FIG. 1B to the closed state shown in FIG. 1A under the action of a biasing force. As shown in FIG. 7, the insertion is accomplished with a snap in action with no need to rotate the rotatable part 40 by hand.

Figure 3A:
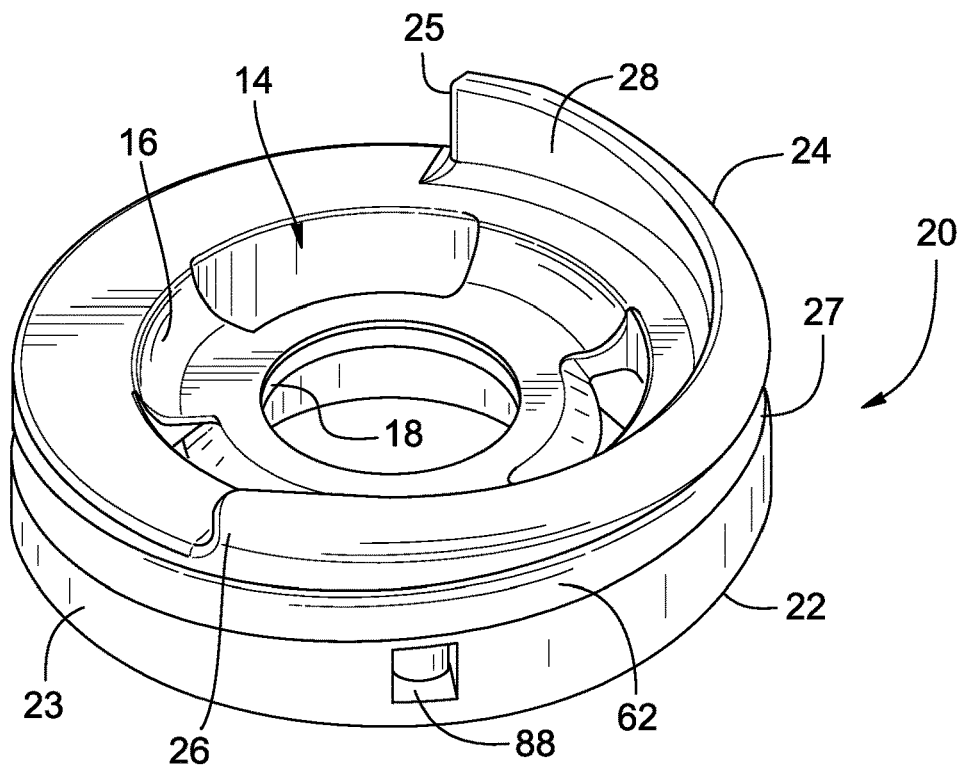
FIG. 3A is a perspective view of a base part of the endoscope eyepiece grasping mechanism of FIGS. 1A and 1B.
Figure 3B:
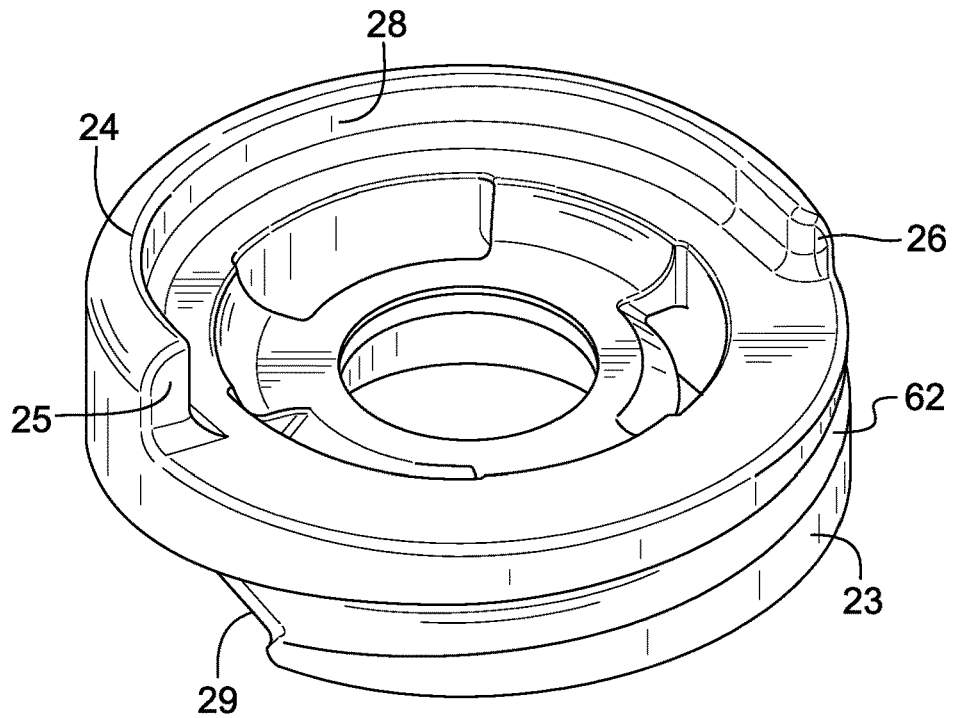
FIG. 3B is a perspective view of the base part of FIG. 3A, rotated counterclockwise by about 180° relative to the view of FIG. 3A.

FIGS. 3A and 3B show the base part 20 detached from the rest of the grasping mechanism 10. The base part 20 defines a lower portion of the interior region 14 which forms the space for the endoscope eyepiece 6, when the endoscope eyepiece 6 is in the coupled (closed) position. The interior region 14 is delimited by a contoured surface 16, that surrounds and defines a radially inward light passage opening 18, and by an inner surface 28 of a base part arcuate wall 24. The arcuate wall 24 is radially outward of the light passage 18 and extends upwardly from a base portion 22 of the base part 20. The base part arcuate wall 24 extends a circumferential distance between a base part arcuate wall portion first circumferential end 25 and a second circumferential end 26. The arcuate wall circumferential ends 25 and 26 define the base part arcuate wall portion wall opening 30.

Figure 4:
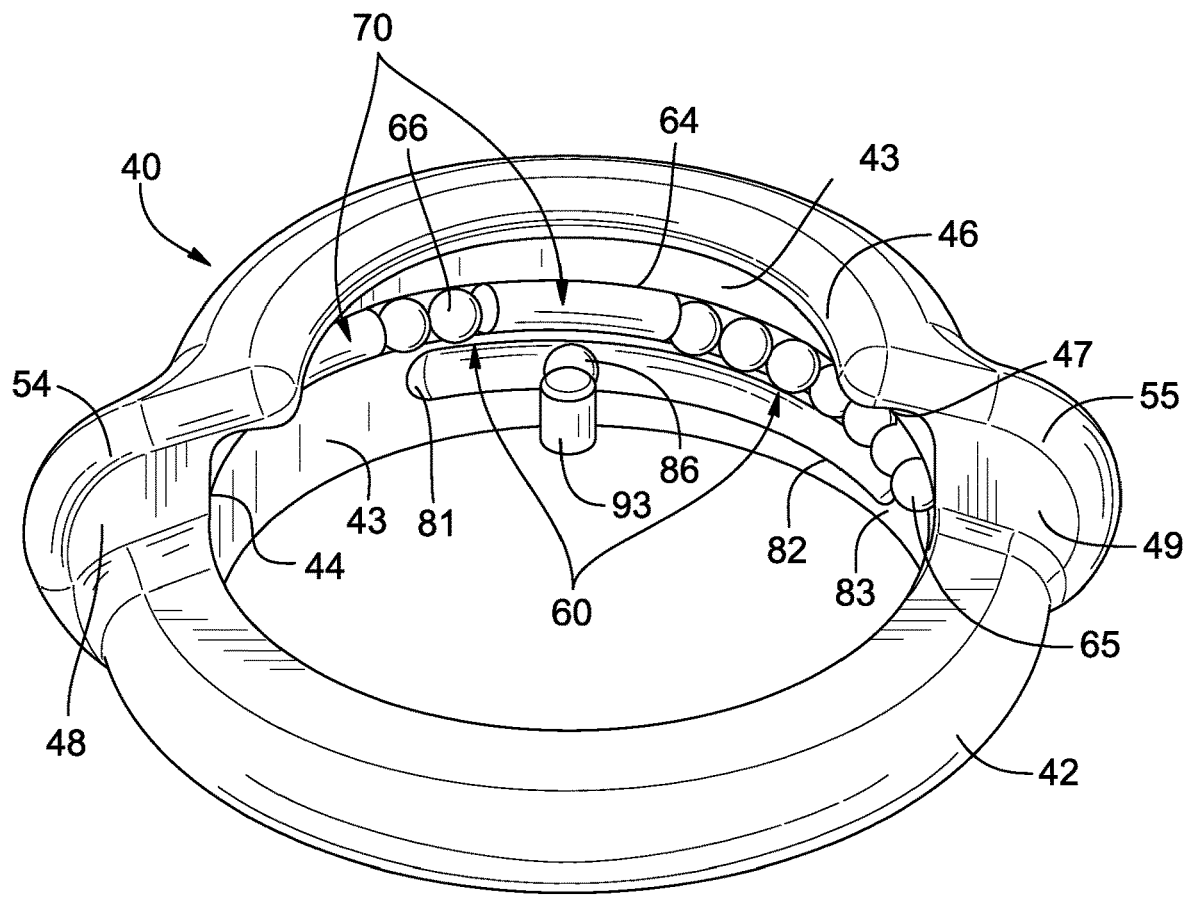
FIG. 4 is a perspective view showing a rotatable part, a ball arrangement (configuration) with balls and a biasing device in a race helical groove, a limit ball, partially in section, in a limit groove, as well as a limit ball support of a limit ball access closure of the endoscope eyepiece grasping mechanism of FIGS. 1A and 1B.

FIG. 4 shows the rotatable part 40 including a lower annular portion 42 that has a radially inward surface 43. The rotatable part 40 further has a rotatable arcuate wall portion 44 that is a continuation of the radially inward surface 43 and that extends axially from the annular portion 42, in an upward direction, as shown in FIG. 4. A radial surface 47 extends radially inwardly from the radially inward surface 43 to an edge 46. The rotatable arcuate wall portion 44 has a circumferential extent between a rotatable part arcuate wall portion first end 48 and a rotatable part arcuate wall portion second end 49. A first grasping flange 54 is provided at the arcuate wall portion first end 48 and a second grasping flange 55 is provided at the arcuate wall portion second end 48.

The grasping mechanism 10 includes a path guide comprising a helical race groove 64 that is provided by the rotatable part 40 (FIG. 4). The path guide also includes a helical groove 62 provided by the base part 20 (FIGS. 3A and 3B) and a ball arrangement or ball configuration 60 with balls 66 and biasing device 70. The helical groove 62 and the helical race groove 64 together form a split helical groove space or cavity that receives the ball arrangement 60. The path guide acts between the base part 20, and the rotatable part 40 for guided movement of the rotatable part 40 relative to the base part 20 for moving the rotatable arcuate wall portion 44 of the rotatable part 40 relative to the base part 20 between the closed state and the open state. As can be seen in FIG. 1B, in the open state, the rotatable part arcuate wall opening 50 and the base part arcuate wall portion wall opening 30 extensively overlap. In addition the path guide acts to change an axial spacing between portions of the rotatable part 40 and the base part 20. A first axial distance D1 and a second axial distance D2 are shown measured from a surface 21 of the base part 20 to the radial surface 47. The first axial distance D1 (FIGS. 1A, 2A) is smaller than the second axial distance D2 (FIGS. 2A and 2B).

Figure 2A:
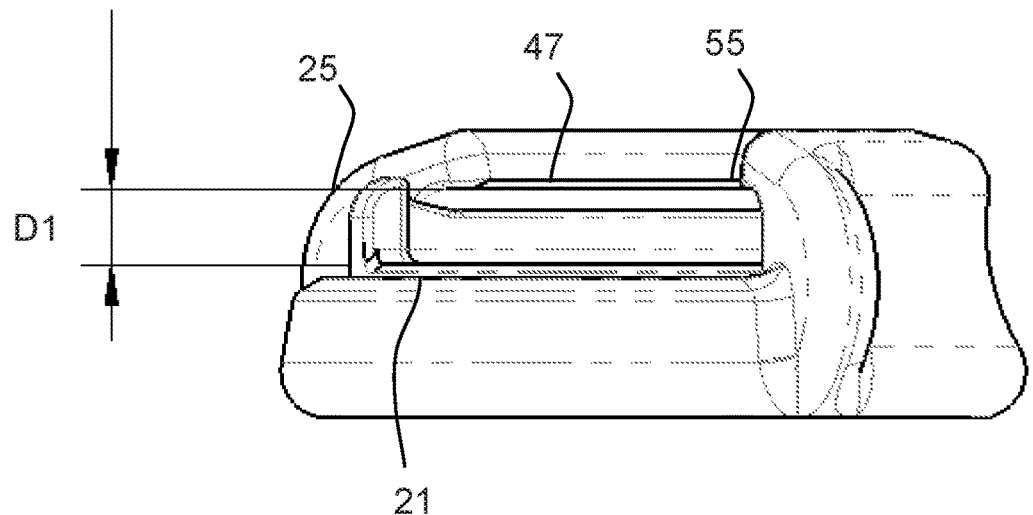
FIG. 2A is a side view showing the endoscope eyepiece grasping mechanism of FIGS. 1A and 1B in the closed state.
Figure 2B:
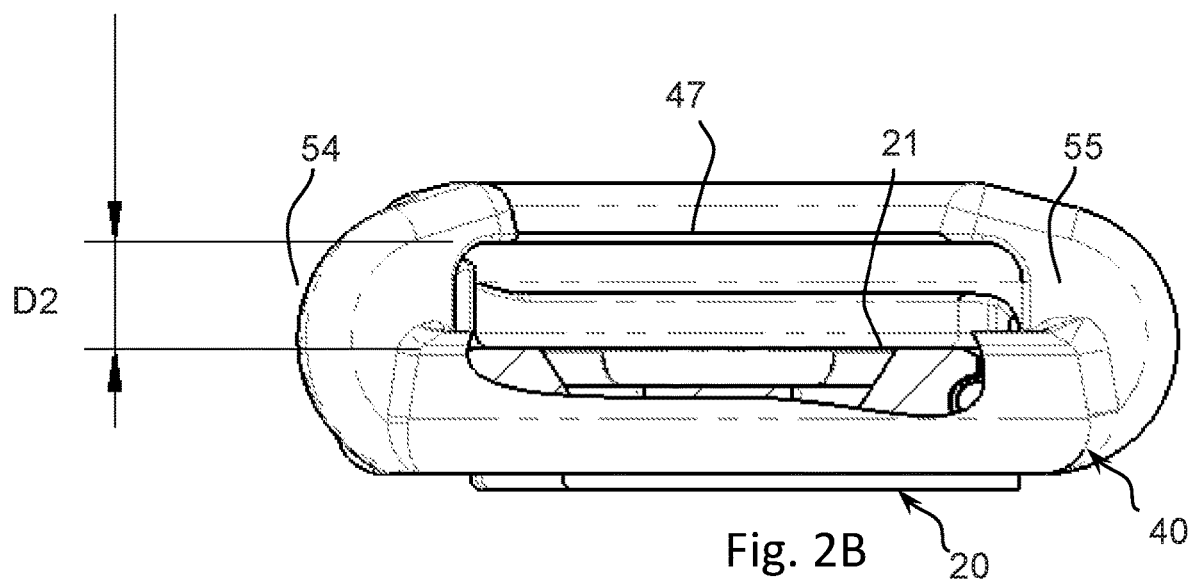
FIG. 2B is a side partially cutaway view showing the endoscope eyepiece grasping mechanism of FIGS. 1A and 1B in the open state.

In the closed state, the radial surface 47 of the rotatable part 40 is spaced from the surface 21 of the base portion 22 by the first axial distance D1 (FIG. 2A). In the open state, the radial surface 47 of the rotatable part 40 is spaced from a surface 21 of the base portion 22 by the second axial distance D2 (FIG. 2B). The first axial distance D1, such as 4.84 mm, is coordinated with the dimensions and shape of the endoscope eyepiece 6 so as to clamp and hold the endoscope eyepiece 6 in the inner space 18, between the radial surface 47 of the rotatable part 40 and the contoured surface 16 of the base part 20, with the grasping mechanism 10 in the closed state. The second axial distance D2, such as 6.75 mm, is sufficient to allow the endoscope eyepiece 6 to be inserted into and removed from the inner space 18, based on sufficient space being provided between the surface 21 and the radial surface 47 to accommodate the passage of the endoscope eyepiece 6 through the overlapping wall openings 30 and 50. This second axial distance D2 is coordinated with the shape of the endoscope eyepiece 6. With the grasping mechanism 10 in the closed state, and the endoscope eyepiece 6 in the coupled position, seated in the contour surface 16 and clamped between the lower radial surface 47 and the contoured surface 16, with a peripheral edge of the endoscope eyepiece 6 in contact with the inner surface 28 of the axial wall 24, the grasping mechanism 10 grasps the endoscope eyepiece 6 to fully retain and hold the endoscope eyepiece 6 from movement relative to the grasping mechanism 10 and the camera head chassis 2.

Figure 5:
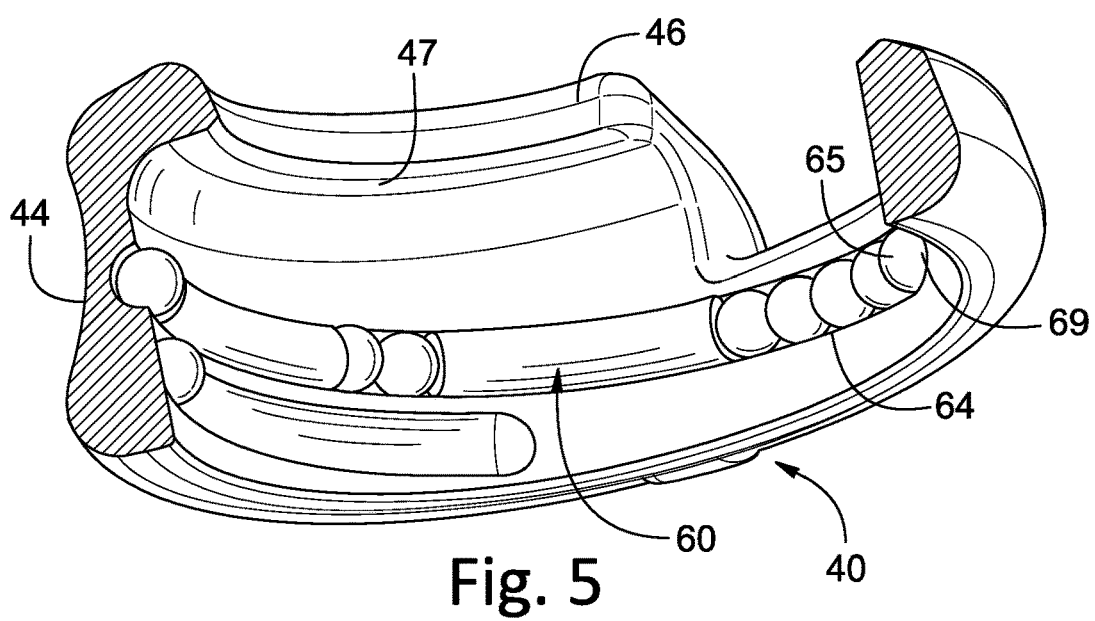
FIG. 5 is a perspective partially sectional view showing the rotatable part with some of the ball arrangement (configuration) in the race helical groove.

The grasping mechanism 10 includes the biasing device 70 that biases the rotatable part for relative movement toward the closed state. In the embodiment shown in the figures, biasing device 70 is integrated into the ball arrangement 60. According to the embodiment shown, the biasing device 70 advantageously comprises one or more compression springs 75. The compression spring 75 are mounted in the helical groove 62 and race groove 64, and act between balls 66. A trailing ball 65 of the ball arrangement 60 interacts with a race groove end 69, as an engagement point with the rotatable part 40, and a leading ball 67 of the ball arrangement 60 interacts with a helical groove end 27, as an engagement point with the base part 20. With the grasping mechanism 10 in the closed state, the compression springs 75 of the biasing device 70, between a leading ball 67 and a trailing ball 65 of the ball arrangement 60, are in a non compressed or less compressed state. With the grasping mechanism 10 in the open state the leading ball 67 (FIG. 6A) of the ball arrangement 60 is positioned at the helical groove end 27 (FIG. 3A) of the base part 20 and the trailing ball 65 is positioned at race groove end 69 of the rotatable part 40 (FIG. 5). In the open state, these ends 27 and 69 are circumferentially closer to each other than in the closed state, such that the compression springs 75 of the biasing device 70 are more compressed. The compressed springs 75 apply a rotational force to rotate the rotatable part 40 clockwise from the open state shown in FIG. 1B to the closed state shown in FIG. 1A.

As can be seen in FIGS. 3A and 3B the helical groove 62 is formed in the outer surface 23 of the base portion 22 of the base part 20. The helical groove 62 extends circumferentially about at least a portion of the base part outer periphery. Although the groove 62 is described as helical or spiral, the groove 62 need not extend fully around the outer periphery of the base portion 22. In the disclosed embodiments the helical groove 62 extends approximately 270° about the circumference of the peripheral surface 23. The race groove 64 is formed in the radially inward surface 43 of the rotatable part 40, particularly at an inner surface of the arcuate wall portion 44.

Figure 6A:
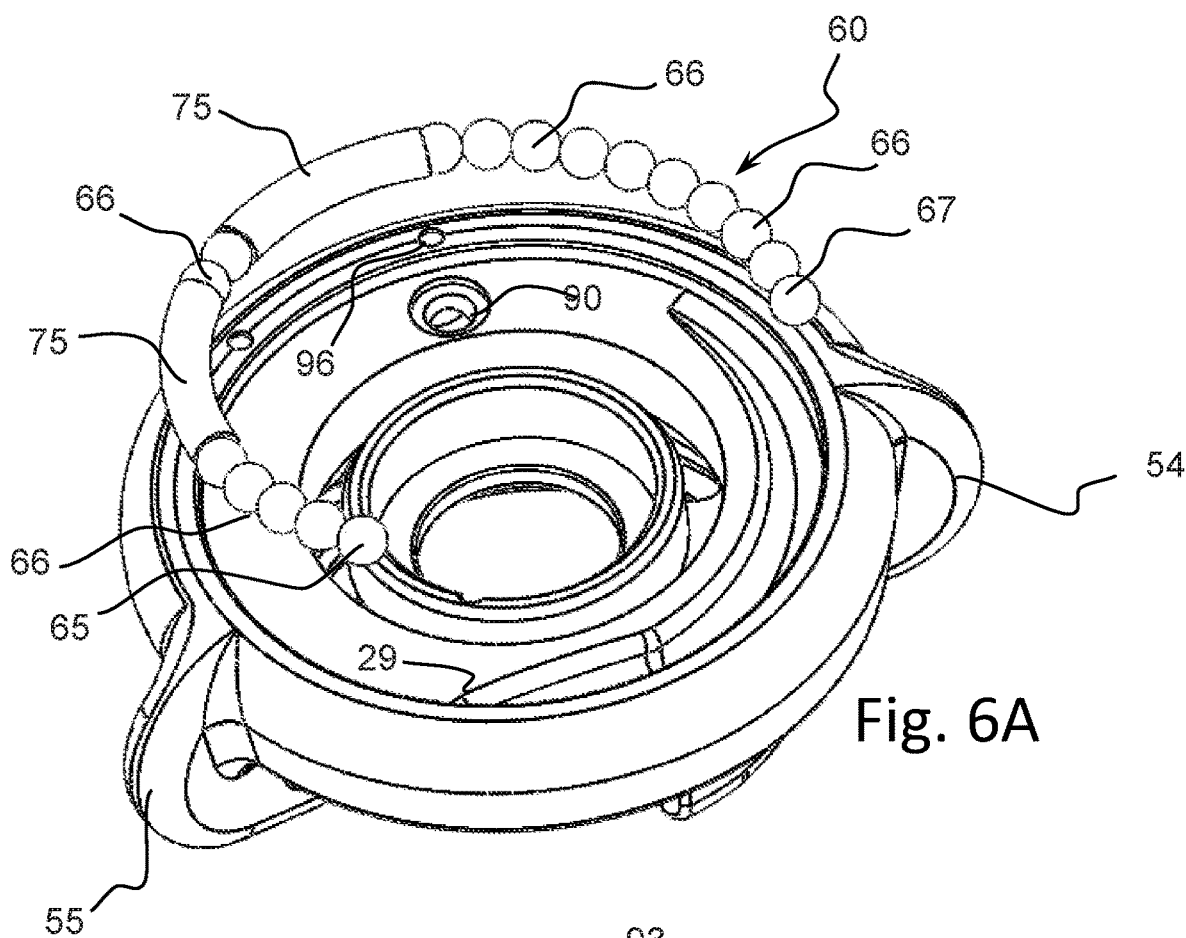
FIG. 6A is a perspective view of a endoscope eyepiece grasping mechanism with the limit ball removed and the base part at a rotational position relative to the rotatable part allowing a loading of the ball arrangement (configuration) and a biasing device into the race groove and showing the ball configuration.

The ball configuration 66 comprises two or more balls 66, preferably a plurality of steel balls 66 in addition to the trailing ball 65 and the leading ball 67. The balls 66 are partially disposed in the race groove 64 and are partially disposed in the helical groove 62. The biasing device 70 advantageously comprises stainless steel compression springs 75 of approximately 38 mm length and 3 mm outer diameter. The balls 65, 66, 67 advantageously comprise approximately thirteen 3 mm stainless steel balls with a configuration as shown in FIG. 6A. With the grasping mechanism 10 in an assembled state, the balls 65, 66, 67 of the ball configuration 60 are captured in the helical groove 62 and in the helical race groove 64 to facilitate the guided rotational and axial movement as described above.

Figure 6B:
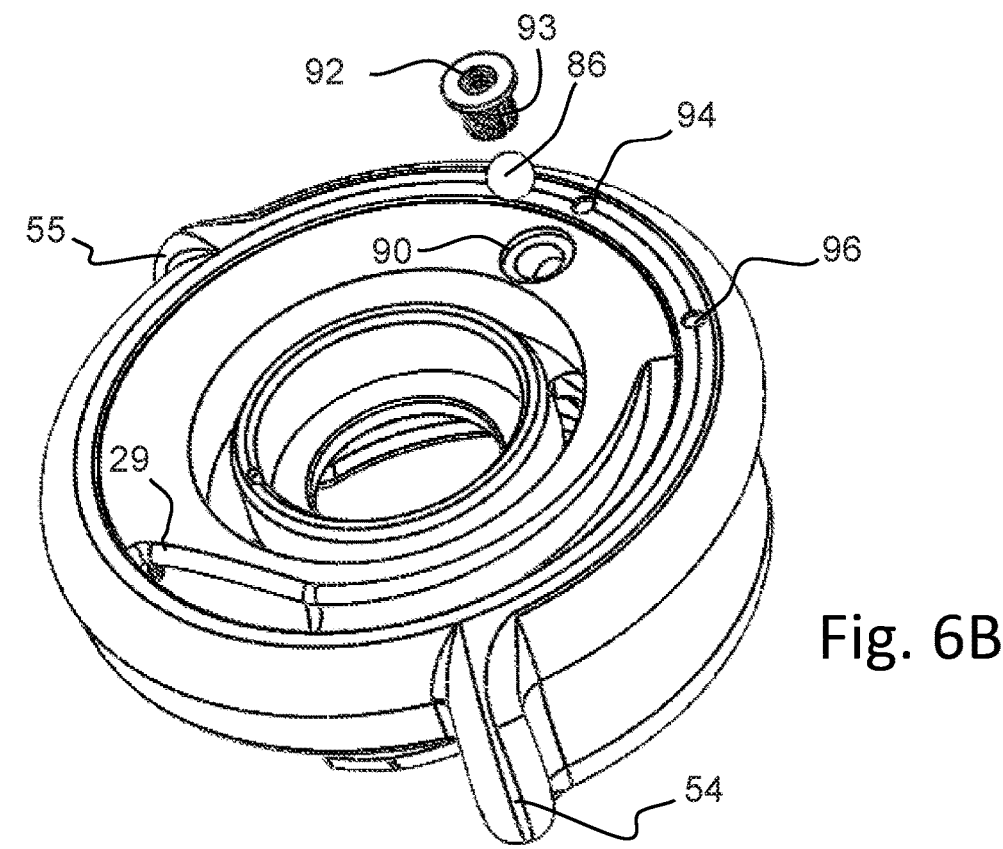
FIG. 6B is a perspective view of a endoscope eyepiece grasping mechanism with the base part at a rotational position relative to the rotatable part to allow the shown limit ball to be inserted into the limit ball access passage, which is to be closed by the limit ball access closure shown.

To assemble the endoscope eyepiece grasping mechanism 10, the base member 20 is placed within the rotatable member 40 and rotated to a position in which a limit ball access passage 90, formed in the base member 20, is aligned with a loading position marker 96 (FIGS. 6A and 6B). This positions a helical groove access edge 29 of the base member 20 relative to the helical groove 62, allowing the balls 65, 66, 67 and compression springs 75 (the ball arrangement 60) to be loaded into the space formed between the helical groove 62 and the race groove 64. The base member 20 is next rotated to a position in which a limit ball access passage 90 is aligned with a use position marker 94 (FIG. 6B). In this position the ball arrangement 60 is retained in space between the helical groove 62 and the race groove 64. The limit ball 86 is next put into the limit ball access passage 90 and a limit ball access closure 92 is pushed into the limit ball access passage 90. This has a limit ball support 93 that supports the limit ball 86 such that the limit ball 86 is partially in a limit ball space 88 (FIG. 3A) of the base part 20 and extends out of the space 88 into a limit helical groove 82 of the rotatable part 40 (FIG. 4). The limit ball access closure 92 is fixed in place by a heat staking to capture the non-removable pin or limit ball support 93, that positions and retains single limiter ball, in the groove 82 and capture all components.

A limit configuration, that limits the rotation of the rotatable part 40 relative to the base part 20, is formed by the limit helical groove 82 which extends essentially parallel to the helical groove 62 along a limited extent of the inner surface 43 of the rotatable part 40. The limited extent of the limit helical groove 82 is defined by a first limit end 81 and a second limit end 83 (FIG. 4). The limit ball 86, disposed partially in the limit ball space 88 and partially in the helical groove 82 is limited to move along the helical groove 82 between the first limit end 81 and the second limit end 83. The limit configuration further includes the limit ball support 93 and the base part that defines the space 88 so as to support the limit ball 86 and hold the limit ball 86 in the location relative to the base part 20.

FIG. 7 shows the camera head 2 with the endoscope eyepiece grasping mechanism 10 along with a positioned endoscope 4. The endoscope 4 has the endoscope eyepiece 6. FIG. 7 also shows a light source connection 7 as well as a signal connection line 8 that is connected to the camera head 2.

The rotatable part 40 advantageously includes the first grasping flange 54 coordinated with the rotatable part arcuate wall portion end 48 and the second grasping flange 55 coordinated with the rotatable part arcuate wall portion end 49. This facilitates the ability to actuate the grasping device 10. For example, while grasping the camera head 2, the user can engage either flange, such as the flange 55, to rotate the rotatable part 40 in the counterclockwise direction to open the grasping mechanism 10 so the endoscope eyepiece 6 may slide in from the side, through the openings 30 and 50 to the interior region 14 of the grasping member 10. A side loading direction SL of the endoscope eyepiece 6 is shown in FIG. 7. Upon releasing the flange 55, the biasing device 70 acts on the rotatable part 40 relative to the base part 20, to rotate the rotatable part 40 back to the closed state as shown in FIG. 1A so as to capture the endoscope eyepiece 6 and retain the endoscope eyepiece 6 under compression spring force with the radial inner surface 47 acting axially towards the base part 20 to retain the endoscope eyepiece 6 in the coupled position.

Figure 8:
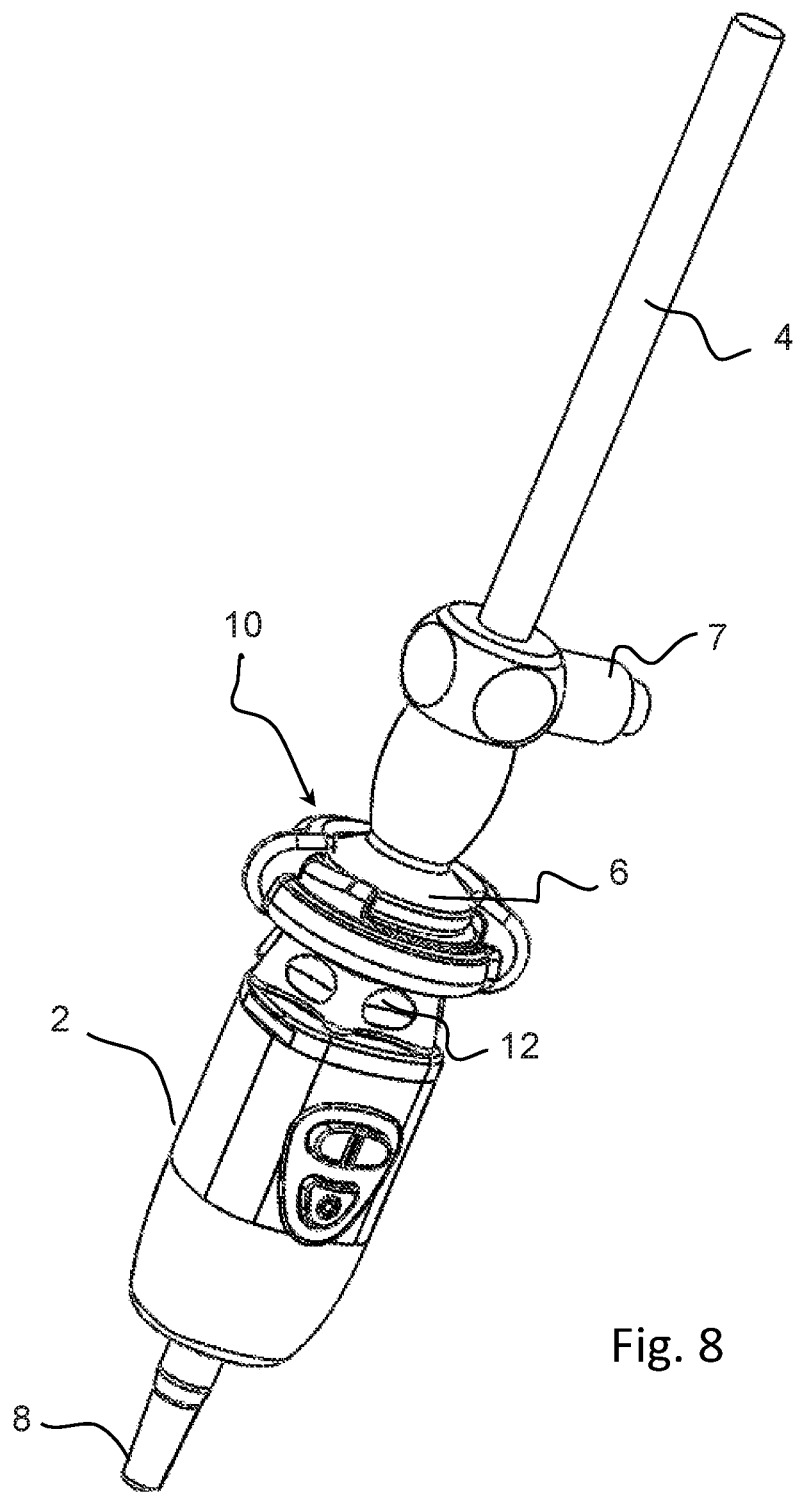
FIG. 8 is a perspective view showing the endoscope having the endoscope eyepiece inserted in the grasping mechanism of the camera head.
Figure 9:
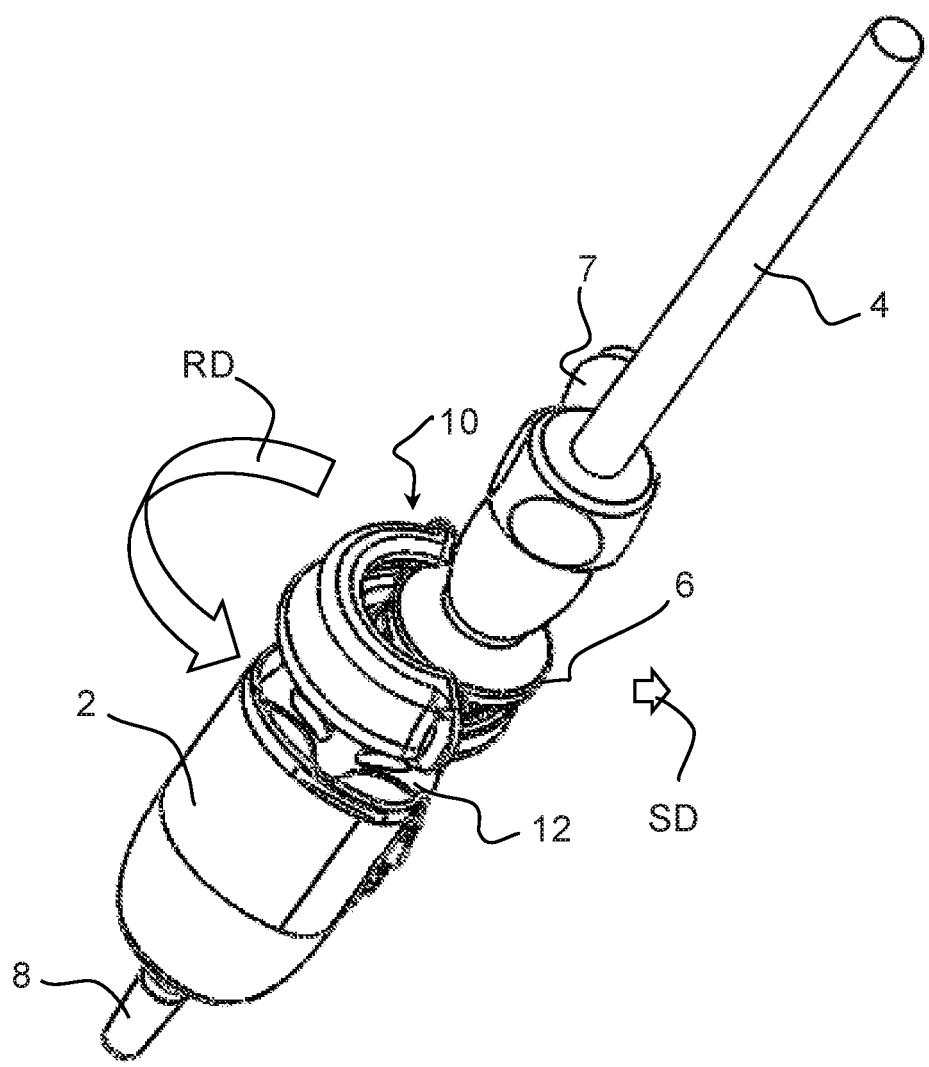
FIG. 9 is a perspective view showing an endoscope, having an endoscope eyepiece, being removed from the grasping mechanism of the camera head.

An aspect of the disclosed embodiment is the configuration which presents a gap G between portions of the axial walls 24 and 44 in the closed state (FIG. 1A), namely the gap G is between the axial wall end 25 of axial wall 24 and the end 49 of rotatable wall portion 44 in the closed state. This gap G and the eyepiece contact surface of the flange 55, at the end 49, are such that the user may simply press the endoscope eyepiece 6 in the region the gap G, particularly pressing the endoscope eyepiece 6 against the flange 55 and wall end 25. This pressing of the endoscope eyepiece 6 at the gap G in the direction SL, as shown in FIG. 7, acts to rotate the rotatable part 40 toward the open state so the endoscope eyepiece 6 slides or snaps in from the side into the coupled position. With this there is no need to grasp the rotatable part with the hands of the user. With the endoscope eyepiece 6 in the coupled position within the interior region 14, it is no longer acting on the rotatable part 40 such that the rotatable part 40 will again rotate clockwise back to the closed state under the force of the biasing device 70 to capture the eyepiece 6. This results in an inserted endoscope as shown in FIG. 8. To remove the endoscope the rotatable part 40 is rotated in direction RD as shown in FIG. 9 and moved in the direction SD.

Each of the base part 20 and the rotatable part 40 is preferably formed as a molded part such as an injection molded part made of plastic material such as PEEK +20% PTFE. After injection molding, further machining can be provided. However, advantageously the molded parts are fully formed by the injection molding process and are formed so as to be ready to be assembled.

Although the structure which follows the path of the one or more grooves is disclosed as balls 65, 66, 67 (steel balls) these may be replaced with another friction reducing material or a member with added seals or other related features. Further other biasing devices may be provided instead of the compression spring arrangement with compression springs 75. For example a coil spring may act between the base part 20 and the rotatable part 40. Further, other limiter configurations may be provided.

While specific embodiments of the invention have been shown and described in detail to illustrate the application of the principles of the invention, it will be understood that the invention may be embodied otherwise without departing from such principles.

LIST OF REFERENCE CHARACTERS 2 camera head chassis
4 endoscope
6 endoscope eyepiece
7 light source connection
8 signal connection line
10 grasping mechanism
12 mounting portion
14 central interior region
16 contoured surface
18 light passage opening
20 base part
21 surface
22 base portion
23 outer peripheral surface
24 base part arcuate wall
25 first circumferential end
26 second circumferential end 27 helical groove end
28 inner surface
29 helical groove access edge
30 base part arcuate wall portion wall opening
40 rotatable part
42 lower annular portion
43 radially inward surface
44 rotatable arcuate wall portion
46 edge
47 radial surface
48 first rotatable part axial wall portion end
49 second rotatable part axial wall portion 2nd
50 rotatable part wall opening
54 first grasping flange
55 second grasping flange
60 ball arrangement or ball configuration
62 helical groove
64 race groove
65 trailing ball
66 balls
67 leading ball
69 race groove end
70 biasing device
75 compression spring
81 first limit end
82 limit helical groove
83 second limit end
86 limit ball
88 limit ball space
90 limit ball access passage
92 limit ball access closure
93 limit ball support
94 use position marker
96 loading position marker
D1 first axial distance
D2 second axial distance
G Gap
SL side loading direction
SD side disconnection direction
RD removal direction of rotation

What is claimed is:

1. An endoscope eyepiece grasping mechanism comprising:
  a base part comprising a base portion with a radially inward light passage and an outer surface and a base part arcuate wall portion disposed radially outward of the light passage, the base part arcuate wall portion extending axially from the base portion and extending a circumferential distance between base part arcuate wall portion circumferential ends and defining a base part arcuate wall portion wall opening between the base part arcuate wall portion circumferential ends;
  a rotatable part with a radially inward surface, the rotatable part comprising an annular portion, and a rotatable arcuate wall portion including an axial surface extending axially from the annular portion, the axial surface including a coupling edge, the rotatable part including a radial surface extending radially inwardly from the axial surface to the coupling edge, the rotatable arcuate wall portion extending a circumferential distance between rotatable part arcuate wall portion circumferential ends and defining a rotatable part arcuate wall opening between the rotatable arcuate wall portion circumferential ends;
  a path guide formed between the base part and the rotatable part for guided movement of the rotatable part relative to the base part for moving the rotatable arcuate wall portion relative to the base part between an open state and a closed state,
  the opened state positioning the rotatable part arcuate wall opening and the base part arcuate wall portion wall opening at least partially overlapping to define an eyepiece receiving spacing and the open state positioning the radial surface of the rotatable part spaced from the base portion by a first axial distance,
  the closed state positioning the rotatable part arcuate wall opening and the base part arcuate wall portion wall opening not overlapping or overlapping to an extent to provide a gap that is smaller than the eyepiece receiving spacing and the closed state positioning the radial surface spaced from the base portion by a second axial distance, which second axial distance is smaller than said first axial distance; and
  a biasing device configured to bias the rotatable part toward the closed state.

2. An endoscope eyepiece grasping mechanism according to claim 1, wherein the path guide comprises:
  a helical groove in the outer surface of the base portion, the helical groove extending circumferentially about at least a portion of a base part outer periphery,
  a helical race groove in the radially inward surface of the rotatable part; and
  a ball configuration comprising a ball partially disposed in the race groove and partially disposed in the helical groove, wherein the ball, the race groove and the helical groove are configured to guide the rotatable part relative to the base part between the open state and the closed state.

3. An endoscope eyepiece grasping mechanism according to claim 2, wherein:
  the base part is an injection molded part with the helical groove formed in the outer surface; and
  the rotatable part is an injection molded part with the race groove formed in the radially inward surface.

4. An endoscope eyepiece grasping mechanism according to claim 2, further comprising a limit configuration configured to limit rotation of the rotatable part relative to the base part in each of two rotational directions, wherein the limit configuration comprises:
  a limit helical groove defined by the rotatable part and extending parallel to the helical race groove of the rotatable part, said limit helical groove having a limited circumferential extent between a first limit end and a second limit end;
  a limit ball; and
  a limit ball support, supporting the limit ball relative to the limit helical groove, whereby the movement of the rotatable part relative to the base part is limited by the travel of the limit ball between the first limit end and the second limit end.

5. An endoscope eyepiece grasping mechanism according to claim 2, wherein the helical groove in the outer surface of the base portion extends less than 360 degrees about a circumference of the base portion.

6. An endoscope eyepiece grasping mechanism according to claim 2, wherein the ball configuration comprises a plurality of balls partially disposed in the race groove and partially disposed in the helical groove.

7. An endoscope eyepiece grasping mechanism according to claim 1, further comprising a limit configuration configured to limit rotation of the rotatable part relative to the base part.

8. An endoscope eyepiece grasping mechanism according to claim 1, wherein the bias device comprises a compression spring.

9. An endoscope eyepiece grasping mechanism according to claim 1, wherein:
the rotatable part has an eyepiece contact surface at one of the arcuate wall portion circumferential ends; and
in the closed state the rotatable part arcuate wall opening and the base part arcuate wall portion wall opening overlap to form the gap in the closed state, whereby upon pressing the endoscope eyepiece toward the gap, the endoscope eyepiece is configured to press the eyepiece contact surface to rotate the rotatable part towards the open state to allow the endoscope eyepiece to be pushed through the eyepiece receiving spacing to the coupled position.

10. An endoscope eyepiece grasping mechanism according to claim 1, wherein the base part is connected to a camera head chassis.

11. A camera head comprising:
a camera head chassis; and
an endoscope eyepiece grasping mechanism according to claim 1, wherein the base part is connected to a camera head chassis.

12. An endoscope system comprising:
an endoscope with an endoscope eyepiece; and
a camera head comprising a camera head chassis and an endoscope eyepiece grasping mechanism according to claim 1, wherein the base part is connected to a camera head chassis.

13. An endoscope eyepiece grasping mechanism according to claim 1, wherein:
the base part, the rotatable part and the biasing device are configured for,
an endoscope eyepiece to be pushed through the eyepiece receiving spacing to a coupled position in the open state,
the rotatable part to rotate to the closed state, and
the radial surface to move axially toward a base position to retain the eyepiece in the coupled position.

* * * * *